US00PP31338P2

(12) United States Plant Patent
Smit

(10) Patent No.: US PP31,338 P2
(45) Date of Patent: Jan. 7, 2020

(54) ***PEPEROMIA* PLANT NAMED 'EC-PEPE-1807'**

(50) Latin Name: *Peperomia obtusifolia*
Varietal Denomination: EC-PEPE-1807

(71) Applicant: Obed Jacob Smit, Sappemeer (NL)

(72) Inventor: Obed Jacob Smit, Sappemeer (NL)

(73) Assignee: Eden Collection B.V., Sappemeer (NL)

( * ) Notice: Subject to any disclaimer, the term of this patent is extended or adjusted under 35 U.S.C. 154(b) by 0 days.

(21) Appl. No.: 16/350,742

(22) Filed: Dec. 31, 2018

(51) Int. Cl.
*A01H 5/12* (2018.01)

(52) U.S. Cl.
USPC ..... Plt./373

(58) Field of Classification Search
USPC ..... Plt./373
CPC ... A01H 6/00; A01H 5/00; A01H 5/02; A01H 5/12
See application file for complete search history.

*Primary Examiner* — Keith O. Robinson

(57) ABSTRACT

A new cultivar of *Peperomia* plant named 'EC-PEPE-1807' that is characterized by bi-colored leaves with green centers surrounded by broad white margins and a compact habit.

1 Drawing Sheet

Botanical classification: *Peperomia obtusifolia.*
Variety denomination: 'EC-PEPE-1807'.

BACKGROUND OF THE INVENTION

The present invention relates to a new and distinct cultivar of *Peperomia* plant botanically known as *Peperomia obtusifolia* and hereinafter referred to by the cultivar name 'EC-PEPE-1807'.

'EC-PEPE-1807' was discovered as a naturally occurring branch mutation of *Peperomia* 'Obtipan' (U.S. Plant Pat. No. 29,598). The new cultivar 'EC-PEPE-1807' was discovered by the inventor in 2015 in a controlled environment in a cultivated area of Sappemeer, Netherlands.

Asexual reproduction of the new cultivar 'EC-PEPE-1807' first occurred by tip cuttings in 2015 in Sappemeer, Netherlands, Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Peperomia* cultivar 'EC-PEPE-1807'. These traits in combination distinguish 'EC-PEPE-1807' as a new and distinct cultivar apart from other existing varieties of *Peperomia* known by the inventor.

1. *Peperomia* 'EC-PEPE-1807' exhibits bi-colored leaves with green centers surrounded by broad white margins.
2. *Peperomia* 'EC-PEPE-1807' exhibits a compact habit.

The closest comparison cultivars are *Peperomia* 'Variegata' (not patented) and *Peperomia* 'Albo-marginata' (not patented). 'EC-PEPE-1807' is distinguishable from 'Variegata' by the following characteristics:

1. *Peperomia* 'EC-PEPE-1807' exhibits bi-colored leaves with solid green centers surrounded by solid broad white margins. In comparison, the leaves of 'Variegata' are more variable in color with discontinuous areas of green and white inter-mixed.

'EC-PEPE-1807' is distinguishable from 'Albo-marginata' by the following characteristics:

1. *Peperomia* 'EC-PEPE-1807' exhibits bi-colored leaves with solid green centers surrounded by solid broad white margins. In comparison, the leaves of 'Albo-marginata' are more variable in color with discontinuous areas of green and white inter-mixed.

'EC-PEPE-1807' is distinguishable from the parent plant *Peperomia* 'Obtipan', by the following characteristics:

1. *Peperomia* 'EC-PEPE-1807' exhibits bi-colored leaves with solid green centers surrounded by solid broad white margins. In comparison, the leaves of the parent plant are green.

BRIEF DESCRIPTION OF THE DRAWING

The accompanying photograph illustrates the distinguishing traits of *Peperomia* 'EC-PEPE-1807'. The photograph shows an overall view of a 22 week old plant. The photograph was taken using conventional techniques and although colors may appear different from actual colors due to light reflectance, it is as accurate as possible by conventional photographic techniques.

BOTANICAL DESCRIPTION OF THE PLANT

The following is a detailed description of the new *Peperomia* cultivar named 'EC-PEPE-1807'. Data was collected in Sappemeer, Netherlands from 22 week old plants grown in a glass greenhouse in 10.5 cm. diameter containers. The time of year was autumn and the temperature range was 18-25 degrees Centigrade during the day and 15-18 degrees Centigrade at night. The light level was natural light level. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'EC-PEPE-1807' has not been tested under all possible conditions and phenotypic differences may be observed with variations in environmental, climatic, and cultural conditions, however, without any variance in genotype.

Botanical classification: *Peperomia obtusifolia* 'EC-PEPE-1807'.
Annual or perennial: Perennial.
Parentage: 'EC-PEPE-1807' is a naturally occurring branch mutation of *Peperomia* 'Obtipan'.
Plant type: Potted plant.
Growth habit: Broad upright.
Plant shape: Globe shaped.
Suitable container size: 7 cm. pots or larger.
Plant height to top of foliage plane: Average 11.8 cm.
Plant width: Average 14.0 cm.
Vigor: Low to moderate.
Growth rate: Low to moderate.
Low temperature tolerance: 10° Centigrade.
High temperature tolerance: 35° Centigrade.
Propagation: Tip cuttings.
Time to initiate roots: Tip cuttings are placed directly in growing containers.
Crop time: Approximately 18 weeks in Summer and 22 weeks in Winter in Sappemeer, Netherlands.
Root system: Fibrous.
Plant fragrance: None.
Stem:
*Branching habit*.—Main branches grow from base with lateral branches.
*Basal branching*.—Yes.
*Pinching*.—Not required.
*Number of main branches per plant*.—Average 1.
*Number of lateral branches per plant*.—Average 1.
*Main branch dimensions*.—Average 6.2 cm. in length and 0.5 cm. in width.
*Internode length*.—0.6 cm.
*Stem appearance*.—Succulent.
*Stem shape*.—Rounded.
*Stem texture*.—Smooth.
*Stem luster*.—Moderately glossy.
*Stem pubescence*.—Absent.
*Stem angle*.—Main branch average 0 degrees from vertical, lateral branch average 40 degrees from main branch.
*Stem strength*.—Moderately strong.
*Stem color* (*young*).—182C, tinged 146C.
*Stem color* (*mature*).—146D, slightly tinged 181C.
*Internode color*.—181C, tinged 146D.
Foliage:
*Leaf arrangement*.—Alternate.
*Compound or single*.—Single.
*Quantity of leaves per lateral branch*.—Average 13.
*Leaf shape*.—Broad elliptic to near orbicular.
*Leaf aspect*.—Slightly to moderately concave.
*Leaf apex*.—Obtuse to rounded.
*Leaf base*.—Broad attenuate.
*Leaf dimensions*.—Average 7.1 cm. in length and 6.5 cm. in width.
*Texture*.—Glabrous, moderately leathery (both surfaces).
*Leaf luster* (*upper surface*).—Glossy.
*Leaf luster* (*lower surface*).—Slightly to moderately glossy.
*Pubescence*.—Absent (both surfaces).
*Leaf margin*.—Entire, very slightly revolute.
*Leaf lobed*.—Not lobed.
*Leaf rugose*.—Not rugose (both surfaces).
*Venation pattern*.—Pinnate, slightly furrowed.
*Young leaf color* (*upper surface*).—137B and 143A to 143B, irregularly broadly margined 150B, outer edge 184D.
*Young leaf color* (*lower surface*).—Between 148D and 191B, irregularly broadly margined 150C, outer edge 184D.
*Mature leaf color* (*upper surface*).—Between N138C and 191A, irregularly broadly margined with a blend of 3D and 154D, outer edge 180C.
*Mature leaf color* (*lower surface*).—Between 148C and 194A, irregularly broadly margined 2D, outer edge 180C.
*Vein color* (*upper surface*).—144A.
*Vein color* (*lower surface*).—141A.
Petiole:
*Petiole appearance*.—Slightly flattened.
*Petiole dimensions*.—Average 1.0 cm. in length, 0.35 cm. in diameter at widest portion, 0.30 cm. in diameter at narrowest portion.
*Petiole texture*.—Glabrous.
*Petiole luster*.—Very slightly glossy on both sides.
*Petiole pubescence*.—Absent.
*Petiole strength*.—Moderate.
*Petiole color* (*upper side*).—180C, moderately tinged 147D.
*Petiole color* (*lower side*).—147D, slightly tinged 180D.
Flower: 'EC-PEPE-1807' has not produced flowers to date.
Fruit and seed: 'EC-PEPE-1807' has not produced fruit or seed to date.
Disease and pest resistance: Disease and pest resistance has not been observed.

The invention claimed is:

1. A new and distinct variety of *Peperomia* plant named 'EC-PEPE-1807' as described and illustrated.

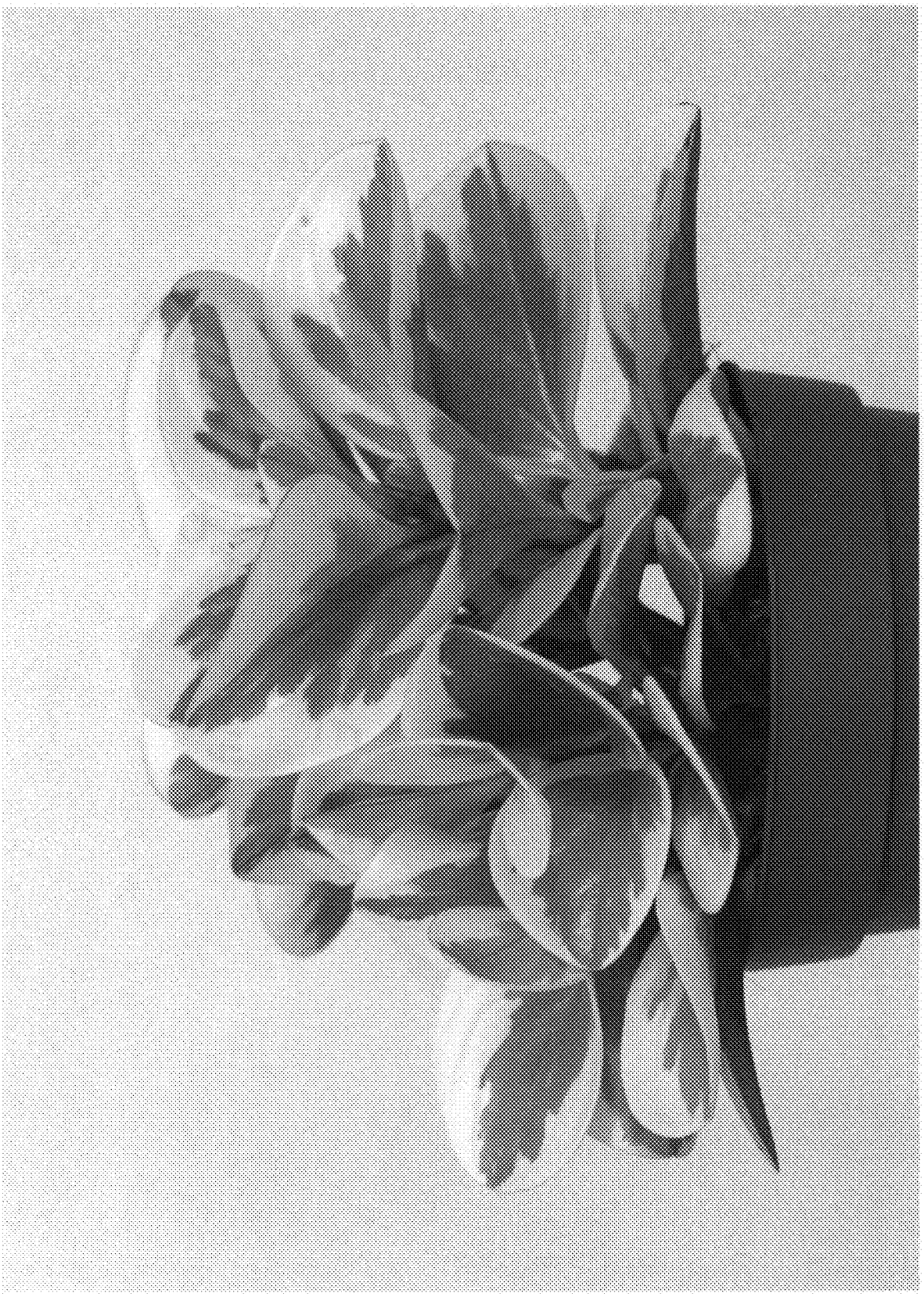

* * * * *